(12) United States Patent
Wang et al.

(10) Patent No.: US 7,097,640 B2
(45) Date of Patent: Aug. 29, 2006

(54) MULTI-FUNCTIONAL SURGICAL CONTROL SYSTEM AND SWITCHING INTERFACE

(75) Inventors: Yulun Wang, Goleta, CA (US);
Charles S. Jordan, Santa Barbara, CA (US); Darrin R. Uecker, Santa Barbara, CA (US)

(73) Assignee: Intuitive Surgical, Inc., Sunnyvale, DE (US)

( * ) Notice: Subject to any disclaimer, the term of this patent is extended or adjusted under 35 U.S.C. 154(b) by 0 days.

(21) Appl. No.: 10/722,837

(22) Filed: Nov. 26, 2003

(65) Prior Publication Data

US 2004/0172011 A1 Sep. 2, 2004

Related U.S. Application Data

(63) Continuation of application No. 08/929,024, filed on Sep. 15, 1997, now abandoned, which is a continuation of application No. 08/711,885, filed on Dec. 23, 1996, now abandoned, which is a continuation of application No. 08/669,629, filed on Jun. 24, 1996, now abandoned.

(51) Int. Cl.
*A61B 18/18* (2006.01)

(52) U.S. Cl. .............. 606/10; 606/13; 606/32; 606/41; 606/46; 704/200; 704/251; 704/275; 600/101; 381/110

(58) Field of Classification Search ............ 606/10–18, 606/32–52; 607/88, 89, 96; 704/3, 4, 233, 704/200–210, 251–255, 270, 275; 600/101–104, 600/106–109, 114, 118; 901/2–9, 30, 36, 901/46; 414/2; 381/110
See application file for complete search history.

(56) References Cited

U.S. PATENT DOCUMENTS

| | | | |
|---|---|---|---|
| 977,825 A | 12/1910 | Murphy | |
| 3,171,549 A | 3/1965 | Orloff | |
| 3,280,991 A | 10/1966 | Melton et al. | |
| 4,058,001 A | 11/1977 | Waxman | |
| 4,128,880 A | 12/1978 | Cray, Jr. | |
| 4,158,750 A | 6/1979 | Sakoe et al. | |
| 4,207,959 A | 6/1980 | Youdin et al. | |
| 4,216,462 A | 8/1980 | McGrath et al. | |
| 4,221,997 A | 9/1980 | Flemming | |
| 4,367,998 A | 1/1983 | Causer | |

(Continued)

FOREIGN PATENT DOCUMENTS

DE  9204118.3  7/1992

(Continued)

OTHER PUBLICATIONS

"A Literature Review: Robots in Medicine" (B. Preising et al.) IEEE Jun. 1991.

(Continued)

*Primary Examiner*—A. Farah

(57) ABSTRACT

An interface which allows a surgeon to operate multiple surgical devices from a single input device. The input device may be a foot pedal that provides output signals to actuate a number of different surgical devices. The surgical devices may include a robotic arm, a laser, an electrocautery device, or an operating table. The interface has an input channel that is coupled to the input device and a plurality of output channels that are coupled to the surgical devices. The interface also has a select input channel which can receive input commands to switch the input channel to one of the output channels. The select channel may be coupled to a speech interface that allows the surgeon to select one of the surgical devices with a voice command. The surgeon can operate any device by providing an input command which switches the input channel to the desired output channel.

13 Claims, 1 Drawing Sheet

U.S. PATENT DOCUMENTS

| | | |
|---|---|---|
| 4,401,852 A | 8/1983 | Noso et al. |
| 4,456,961 A | 6/1984 | Price et al. |
| 4,460,302 A | 7/1984 | Moreau et al. |
| 4,474,174 A | 10/1984 | Petruzzi |
| 4,491,135 A | 1/1985 | Klein |
| 4,503,854 A | 3/1985 | Jako |
| 4,517,963 A | 5/1985 | Michel |
| 4,523,884 A | 6/1985 | Clement et al. |
| 4,586,398 A | 5/1986 | Yindra |
| 4,604,016 A | 8/1986 | Joyce |
| 4,616,637 A | 10/1986 | Caspari et al. |
| 4,624,011 A | 11/1986 | Watanabe et al. |
| 4,633,389 A | 12/1986 | Tanaka et al. |
| 4,635,292 A | 1/1987 | Mori et al. |
| 4,641,292 A | 2/1987 | Tunnell et al. |
| 4,655,257 A | 4/1987 | Iwashita |
| 4,672,963 A | 6/1987 | Barken |
| 4,676,243 A | 6/1987 | Clayman |
| 4,728,974 A | 3/1988 | Nio et al. |
| 4,750,136 A | 6/1988 | Arpin |
| 4,762,455 A | 8/1988 | Coughlan et al. |
| 4,776,016 A | 10/1988 | Hansen |
| 4,791,934 A | 12/1988 | Brunnett |
| 4,791,940 A | 12/1988 | Hirschfeld et al. |
| 4,794,912 A | 1/1989 | Lia |
| 4,807,273 A | 2/1989 | Haendle |
| 4,815,006 A | 3/1989 | Andersson et al. |
| 4,815,450 A | 3/1989 | Patel |
| 4,817,050 A | 3/1989 | Komastsu |
| 4,837,734 A | 6/1989 | Ichikawa et al. |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,930,494 A | 6/1990 | Takehana et al. |
| 4,945,479 A | 7/1990 | Rusterholz et al. |
| 4,949,717 A | 8/1990 | Shaw |
| 4,954,952 A | 9/1990 | Ubhayakar et al. |
| 4,965,417 A | 10/1990 | Massie |
| 4,969,709 A | 11/1990 | Sogawa et al. |
| 4,969,890 A | 11/1990 | Sugita et al. |
| 4,979,933 A | 12/1990 | Runge |
| 4,979,949 A | 12/1990 | Matsen, III et al. |
| 4,980,626 A | 12/1990 | Hess et al. |
| 4,989,253 A | 1/1991 | Liang et al. |
| 4,996,975 A | 3/1991 | Nakamura |
| 5,019,968 A | 5/1991 | Wang et al. |
| 5,020,001 A | 5/1991 | Yamamoto et al. |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,105,367 A | 4/1992 | Tsuchihashi et al. |
| 5,109,499 A | 4/1992 | Inagami et al. |
| 5,123,095 A | 6/1992 | Papadopulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,166,513 A | 11/1992 | Keenan et al. |
| 5,175,694 A | 12/1992 | Amato |
| 5,182,641 A | 1/1993 | Diner et al. |
| 5,184,601 A | 2/1993 | Putman |
| 5,187,574 A | 2/1993 | Kosemura et al. |
| 5,196,688 A | 3/1993 | Hesse et al. |
| 5,201,325 A | 4/1993 | McEwen et al. |
| 5,201,743 A | 4/1993 | Haber et al. |
| 5,217,003 A | 6/1993 | Wilk |
| 5,221,283 A | 6/1993 | Chang |
| 5,228,429 A | 7/1993 | Hatano |
| 5,230,023 A | 7/1993 | Nakano |
| 5,230,623 A | 7/1993 | Guthrie et al. |
| 5,236,432 A | 8/1993 | Matsen, III et al. |
| 5,249,121 A | 9/1993 | Baum et al. |
| 5,251,127 A | 10/1993 | Raab |
| 5,257,999 A | 11/1993 | Slanetz, Jr. |
| 5,271,384 A | 12/1993 | McEwen et al. |
| 5,274,862 A | 1/1994 | Palmer, Jr. et al. |
| 5,279,309 A | 1/1994 | Taylor et al. |
| 5,282,806 A | 2/1994 | Haber |
| 5,289,273 A | 2/1994 | Lang |
| 5,289,365 A | 2/1994 | Caldwell et al. |
| 5,299,288 A | 3/1994 | Glassman et al. |
| 5,300,926 A | 4/1994 | Stoeckl |
| 5,303,148 A | 4/1994 | Mattson et al. |
| 5,304,185 A | 4/1994 | Taylor |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,335,313 A | 8/1994 | Douglas |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,372,147 A | 12/1994 | Lathrop, Jr. et al. |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,408,409 A | 4/1995 | Glassman et al. |
| 5,410,638 A | 4/1995 | Colgate et al. |
| 5,417,210 A | 5/1995 | Funda et al. |
| 5,417,701 A | 5/1995 | Holmes |
| 5,422,521 A | 6/1995 | Neer et al. |
| 5,431,645 A | 7/1995 | Smith et al. |
| 5,434,457 A | 7/1995 | Josephs et al. |
| 5,436,542 A | 7/1995 | Petelin et al. |
| 5,442,728 A | 8/1995 | Kaufman et al. |
| 5,443,384 A | 8/1995 | Franseen et al. |
| 5,445,166 A | 8/1995 | Taylor |
| 5,451,924 A | 9/1995 | Massimino et al. |
| 5,455,766 A | 10/1995 | Scheller et al. |
| 5,458,547 A | 10/1995 | Teraoka et al. |
| 5,458,574 A | 10/1995 | Machold et al. |
| 5,476,010 A | 12/1995 | Fleming et al. |
| 5,482,073 A | 1/1996 | Winnie et al. |
| 5,490,117 A | 2/1996 | Oda et al. |
| 5,490,843 A | 2/1996 | Hildwein et al. |
| 5,500,854 A | 3/1996 | Uotila |
| 5,506,912 A | 4/1996 | Nagasaki et al. |
| 5,511,256 A | 4/1996 | Capaldi |
| 5,512,919 A | 4/1996 | Araki |
| 5,515,478 A | 5/1996 | Wang |
| 5,544,654 A | 8/1996 | Murphy et al. |
| 5,553,198 A | 9/1996 | Wang et al. |
| 5,562,503 A | 10/1996 | Ellman et al. |
| 5,566,272 A | 10/1996 | Brems et al. |
| 5,571,110 A | 11/1996 | Matsen, III et al. |
| 5,572,999 A | 11/1996 | Funda et al. |
| 5,609,560 A | 3/1997 | Ichikawa et al. |
| 5,626,595 A | 5/1997 | Sklar et al. |

| | | |
|---|---|---|
| 5,627,584 A | 5/1997 | Nishikori et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,640,953 A | 6/1997 | Bishop et al. |
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |
| 5,695,500 A | 12/1997 | Taylor et al. |
| 5,696,574 A | 12/1997 | Schwaegerle |
| 5,696,837 A | 12/1997 | Green |
| 5,713,350 A | 2/1998 | Yokota et al. |
| 5,715,548 A | 2/1998 | Weismiller et al. |
| 5,715,823 A | 2/1998 | Wood |
| 5,718,038 A | 2/1998 | Takiar et al. |
| 5,727,569 A | 3/1998 | Benetti et al. |
| 5,729,659 A | 3/1998 | Potter |
| 5,735,290 A | 4/1998 | Sterman et al. |
| 5,737,711 A | 4/1998 | Abe |
| 5,749,362 A | 5/1998 | Funda et al. |
| 5,754,741 A | 5/1998 | Wang et al. |
| 5,762,458 A | 6/1998 | Wang et al. |
| 5,771,511 A | 6/1998 | Kummer et al. |
| 5,774,841 A | 6/1998 | Salazar et al. |
| 5,776,126 A | 7/1998 | Wilk et al. |
| 5,779,623 A | 7/1998 | Bonnell |
| 5,788,688 A | 8/1998 | Bauer et al. |
| 5,792,135 A | 8/1998 | Madhani et al. |
| 5,792,178 A | 8/1998 | Welch et al. |
| 5,797,900 A | 8/1998 | Madhani et al. |
| 5,800,423 A | 9/1998 | Jensen |
| 5,802,467 A | 9/1998 | Salazar et al. |
| 5,807,284 A | 9/1998 | Foxlin |
| 5,807,377 A | 9/1998 | Madhani et al. |
| 5,807,378 A | 9/1998 | Jensen et al. |
| 5,808,665 A | 9/1998 | Green |
| 5,809,591 A | 9/1998 | Capaldi et al. |
| 5,810,880 A | 9/1998 | Jensen et al. |
| 5,812,978 A | 9/1998 | Nolan |
| 5,813,813 A | 9/1998 | Daum et al. |
| 5,814,038 A | 9/1998 | Jensen et al. |
| 5,817,084 A | 10/1998 | Jensen |
| 5,825,982 A | 10/1998 | Wright et al. |
| 5,836,869 A | 11/1998 | Kudo et al. |
| 5,841,950 A | 11/1998 | Wang et al. |
| 5,844,824 A | 12/1998 | Newman et al. |
| 5,855,583 A | 1/1999 | Wang et al. |
| 5,857,967 A | 1/1999 | Frid et al. |
| 5,859,934 A | 1/1999 | Green |
| 5,860,995 A | 1/1999 | Berkelaar |
| 5,876,325 A | 3/1999 | Mizuno et al. |
| 5,877,819 A | 3/1999 | Branson |
| 5,878,193 A | 3/1999 | Wang et al. |
| 5,882,206 A | 3/1999 | Gillio |
| 5,884,350 A | 3/1999 | Kurze |
| 5,887,121 A | 3/1999 | Funda et al. |
| 5,895,461 A | 4/1999 | De La Huerga |
| 5,897,498 A | 4/1999 | Canfield et al. |
| 5,924,074 A | 7/1999 | Evans |
| 5,931,832 A | 8/1999 | Jensen |
| 5,950,629 A | 9/1999 | Taylor et al. |
| 5,970,457 A | 10/1999 | Brant et al. |
| 5,971,976 A | 10/1999 | Wang et al. |
| 5,976,156 A | 11/1999 | Taylor et al. |
| 6,024,695 A | 2/2000 | Taylor et al. |
| 6,080,181 A | 6/2000 | Jensen et al. |
| 6,102,850 A * | 8/2000 | Wang et al. ............ 600/102 |
| 6,201,984 B1 | 3/2001 | Funda et al. |
| 6,224,542 B1 | 5/2001 | Chang et al. |
| 6,278,975 B1 * | 8/2001 | Brant et al. ............ 704/275 |
| 6,463,361 B1 | 10/2002 | Wang et al. |
| 6,496,099 B1 | 12/2002 | Wang et al. |
| 6,640,145 B1 * | 10/2003 | Hoffberg et al. ............ 700/83 |
| 6,642,836 B1 | 11/2003 | Wang et al. |
| 6,646,541 B1 | 11/2003 | Wang et al. |
| 6,788,999 B1 * | 9/2004 | Green ............ 700/275 |
| 6,850,817 B1 | 2/2005 | Green |

FOREIGN PATENT DOCUMENTS

| | | |
|---|---|---|
| DE | 4310842 C2 | 1/1995 |
| EP | 0239409 A1 | 9/1987 |
| EP | 0424687 A1 | 5/1991 |
| EP | 0776738 A2 | 6/1997 |
| FR | 2642882 | 8/1990 |
| WO | WO 91/04711 | 4/1991 |
| WO | WO 92/20295 | 11/1992 |
| WO | WO 93/13916 | 7/1993 |
| WO | WO 94/18881 | 9/1994 |
| WO | WO 94/26167 | 11/1994 |
| WO | 95/01757 | 1/1995 |
| WO | 96/09587 | 3/1996 |
| WO | WO 97/15240 | 5/1997 |
| WO | 98/25666 | 6/1998 |
| WO | 99/21165 | 4/1999 |
| WO | 99/42029 | 8/1999 |

OTHER PUBLICATIONS

"A New Microsurgical Robot System for Corneal Transplantation" (Noriyuki Tejima), Precision Machinery 1988.

"A New System for Computer Assisted Neurosurgery" (S. Lavallee), IEEE 1989.

"A Robot in an Operating Room: A Bull in a China Shop" (J.M. Dolan et al.), IEEE 1987.

"An Advanced Control Micromanipulator for Surgical Applications" (Ben Gayed et al.), Systems Science vol. 13 1987.

"Analysis of the Surgeon's Grasp for Telerobotic Surgical Manipulation" (Frank Tendick and Lawrence Stark), IEEE 1989.

"Anthropomorphic Remote Manipulator", NASA Tech Briefs 1991.

"Controlling Remote Manipulators through Kinesthetic Coupling" (A.K. Bejczy), Computers in Mechanical Engineering 1983.

"Design of a Surgeon-Machine Interface for Teleoperated Microsurgery" (Steve Charles M.D. et al.), IEEE 1989.

"Force Feedback-Based Telemicromanipulation for Robot Surgery on Soft Tissues" (A.M. Sabatini et al.), IEEE 1989.

"Human/Robot Interaction via the Transfer of Power and Information Signals—Part I: Dynamics and Control Analysis" (H. Kazerooni), IEEE 1989.

"Human/Robot Interaction via the Transfer of Power and Information Signals—Part II: An Experimental Analysis" (H. Kazerooni), IEEE 1989.

"Kinematic Control and Visual Display of Redundant Teleoperators" (Hardi Das et al.), IEEE 1989.

"Motion Control for a Sheep Shearing Robot" (James P. Trevelyan et al.), Proceedings of the 1st International Symposium on Robotics Research, MIT, Cambridge, Massachusetts, USA,1983.

"On a Micro-Manipulator for Medical Application—Stability Consideration of its Bilateral Controller" (S. Majima et al.), Mechatronics 1991.

"Power and Impedance Scaling in Bilateral Manipulation" (J. Edward Colgate), IEEE 1991.

"Properties of Master-Slave Robots" (C. Vibet), Motor-con 1987.

"Robots and Telechirs" (M.W. Thring), Wiley 1983.

"Robots for the Operating Room" (Elizabeth Corcoran), The New York Times, Sunday Jul. 19, 1992, Section 3, p. 9, col. 1.

"S.M.O.S.: Stereotaxical Microtelemanipulator for Ocular Surgery" (Aicha Guerrouad and Pierre Vidal), IEEE 1989.

"Six-Axis Bilateral Control of an Articulated Slave Manipulator Using a Cartesian Master Manipulator" (Masao Inoue), Advanced Robotics 1990.

"Surgery in Cyberspace" (Taubes), Discover Magazine, Dec. 1994.

"Taming the Bull: Safety in a Precise Surgical Robot" (Russell H. Taylor et al.), IEEE 1991.

Abstract of a presentation "3-D Vision Technology Applied to Advanced Minimally Invasive Surgery Systems" given at the 3rd World Congress of Endoscopic Surgery in Bordeaux, Jun. 18-20, 1992 "Session 15/3" (1 page total).

Abstract of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992 (1 page total).

Abstract of a presentation "Camera Control for Laparoscopic Surgery by Speech-Recognizing Robot: Constant Attention and Better Use of Personnel" (Colin Besant et al.) given at the 3rd World Congress of Endoscopic Surgery in Bordeaux, Jun. 18-20, 1992 (1 page total).

Abstract of a presentation "Concept and Experimental Application of a Surgical Robotic System the Steerable MIS Instrument SMI" given at the 3rd World Congress of Endoscopic Surgery in Bordeaux, Jun. 18-20, 1992 (1 page total).

Abstract of a presentation "Design Considerations of a New Generation Endoscope Using Robotics and Computer Vision Technology" (S.M. Krishnan et al.) given at the 3rd World Congress of Endoscopic Surgery in Bordeaux, Jun. 18-20, 1992 (1 page total).

Abstract of a presentation "Telepresence: Advanced Teleoperator Technology for Minimally Invasive Surgery", (P. Green et al.) given at "Medicine meets virtual reality" symposium in San Diego, Jun. 4-7, 1992 (20 pages total).

Abstract of a presentation given at the 3rd World Congress of Endoscopic Surgery in Bordeaux, Jun. 18-20, 1992, entitled "Session 15/1" (1 page total).

Abstract of a presentation given at the 3rd World Congress of Endoscopic Surgery in Bordeaux (Jun. 18 to 20, 1992), entitled "Session 15/2" (1 page total).

Abstract of a presentation given at the 3rd World Congress of Endoscopic Surgery in Bordeaux (Jun. 18 to 20, 1992), entitled Session 15/4 (1 page total).

Abstract of a presentation given at the 3rd World Congress of Endoscopic Surgery in Bordeaux (Jun. 18 to 20, 1992), entitled "Session 15/5" (1 page total).

Abstract of a presentation 'Telepresence: Advanced Teleoperator Technology for Minimally Invasive Surgery (P. Green et al.) given at the 3rd World Congress of Endoscopic Surgery in Bordeaux, Jun. 18-20, 1992 (2 pages total).

Industrial Robotics (Gordon M. Mair), Prentice Hall 1988 (pp. 41-43, 49-50, 54, 203-209 enclosed).

Statutory Declaration of Dr. Philip S. Green, presenter of the video entitled "Telepresence Surgery—The Future of Minimally Invasive Medicine".

Transcript of a video presented by SRI at the 3rd World Congress of Endoscopic Surgery in Bordeaux on Jun. 18-20, 1992, in Washington on Apr. 9, 1992, and in San Diego, CA on Jun. 4-7, 1992 entitled "Telepresence Surgery—The Future of Minimally Invasive Medicine".

Wolf et al. (1990) "Student Reference Manual for Electronic Instrumentation Laboratories," 498-499.

Alexander, "A Survey Study of Teleoperators, Robotics, and Remote Systems Technology", Remotely Manned Systems—Exploration and Operation in Space, California Institute of Technology 1973.

Alexander, "Impacts of Telemation on Modern Society", On the Theory and Practice of Robots and Manipulators vol. II, 1974.

Guerrouad, "Voice Control in the Surgery Room," IEEE Engineering in Medicine & Biology Society 11th Annual International Conference 1989 (2 pages total).

Rasor et al., "Endocorporeal Surgery Using Remote Manipulators", Remotely Manned Systems—Exploration and Operation in Space, California Institute of Technology 1973.

Stryker Endoscopy, "Sidne", Operating and Maintenance Manual, 33 pages total.

Wilson et al., "Filmless PACS in a multiple facility environment," Proceedings of the Spie, Spie, Bellingham, VA, US vol. 2711, pp. 500-509 (XP002082137).

* cited by examiner

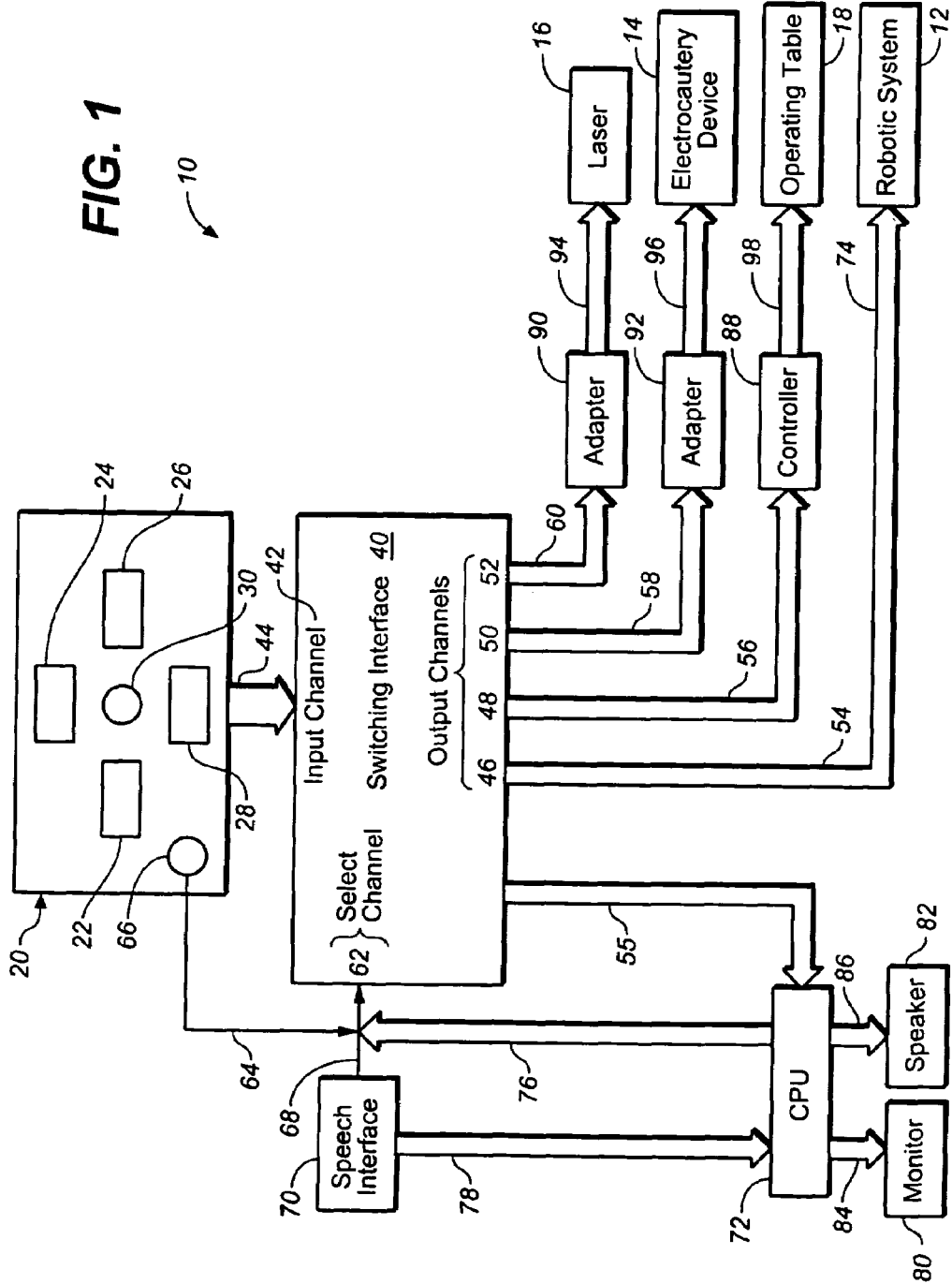

MULTI-FUNCTIONAL SURGICAL CONTROL SYSTEM AND SWITCHING INTERFACE

This application is a CON of Ser. No. 08/929,024 Sep. 15, 1997, which is a CON of Ser. No. 08/771,885 Dec. 23, 1996, which is a CON of Ser. No. 08/669,629 Jun. 24, 1996, all of which are now abandoned.

BACKGROUND OF THE INVENTION

1. Field of the Invention

The present invention generally relates to control systems. More particularly, the present invention relates to an interface that allows multiple surgical devices to be controlled from an input device, such as a foot pedal.

2. Description of Related Art

Many surgical procedures are performed with multiple instruments. For example, some laparoscopic procedures are performed utilizing a robotic arm system produced by Computer Motion, Inc. of Goleta, Calif. to hold and move an endoscope. The surgeon may also use a laser to cut tissue and an electrocautery device to cauterize the tissue. Each instrument has a unique control panel or foot pedal to operate the device. The surgeon must therefore depress one foot pedal to move the robotic arm and endoscope, depress a different foot pedal to actuate the electrocautery device, and manipulate yet another input device to energize the laser. Operating multiple input devices may distract the surgeon, thereby reducing the efficiency and safety of performing the procedure. It would therefore be desirable to provide an interface that would allow the surgeon to select and control multiple surgical devices from a single input device. Additionally, it is also desirable to provide an interface that would allow the surgeon to mutually exclusively select and control multiple surgical devices from an input device.

SUMMARY OF THE INVENTION

The present invention provides an interface for coupling an input device to a first surgical apparatus and a second surgical apparatus, the interface comprising:

(a) a first input channel coupled to the input device;

(b) a first output channel coupled to the first surgical apparatus;

(c) a second output channel coupled to the second surgical apparatus;

(d) a select channel configured to switch said first input channel between said first output channel and said second output channel.

The interface allows a surgeon to operate multiple surgical devices from a single input device. The input device may be a foot pedal that provides output signals to actuate a number of different surgical devices. The surgical devices may include a robotic arm system, a laser, an electrocautery device, or an operating table. The interface has an input channel that is coupled to the input device and a plurality of output channels that are coupled to the surgical devices. The interface also has a select channel which can receive input commands and correspondingly switch the input channel between one of the output channels. The select channel may be coupled to a speech interface that allows the surgeon to select one of the surgical devices with a voice command. The surgeon can then operate a specific device after providing an input or switching command which switches the input channel to the desired output channel and thereby connects the input device with the desired surgical device.

BRIEF DESCRIPTION OF THE DRAWINGS

The objects and advantages of the present invention will be readily apparent to those ordinarily skilled in the art after reviewing the following detailed description and accompanying drawings, wherein:

FIG. 1 is a schematic of a control system and interface in accordance with the present invention.

DETAILED DESCRIPTION OF THE INVENTION

Referring to drawings more particularly by reference numbers, FIG. 1 shows a surgical system 10 in accordance with the present invention. The system 10 allows a surgeon to operate a number of different surgical devices 12, 14, 16 and 18 from a single input device 20. Providing a single input device reduces the complexity of operating the various devices and improves the efficiency of a surgical procedure performed by a surgeon.

Surgical device 12 may be a robotic arm which can hold and move a surgical instrument. The arm 12 may be a device such as that sold by Computer Motion, Inc. of Goleta, Calif. a under the trademark AESOP. The arm 12 is commonly used to hold and move an endoscope within a patient. The system of the present invention allows the surgeon to control the operation of the robotic arm 12 through the input device 20.

Surgical device 14 may be an electrocautery device. Electrocautery devices typically have a bi-polar tip which carries a current that heats and denatures tissue. The device is typically coupled to an on-off switch to actuate the device and heat the tissue. The electrocautery device may also receive control signals to vary its power output. The system 10 of the present invention allows the surgeon to control the operation of the electrocautery device through the input device 20.

Surgical device 16 may be a laser. The laser 16 may be actuated through an on-off switch. Additionally, the power of the laser 16 may be controlled by control signals. The system 10 of the present invention allows the surgeon to control the operation of the laser 16 through the input device 20.

Device 18 may be an operating table. The operating table 18 may contain motors and mechanisms which adjust the position of the table. The present invention allows the surgeon to control the position of the table 18 through the input device 20. Although four surgical devices 12, 14, 16 and 18 are described, it is to be understood that other functions within the operating room may be controlled through the input device 20. By way of example, the system 10 may allow the surgeon to control the lighting and temperature of the operating room through the input device 20.

The input device 20 may be a foot pedal which has a plurality of buttons 22, 24, 26, 28 and 30 that can be depressed by the surgeon. Each button is typically associated with a specific control command of a surgical device. For example, when the input device 20 is controlling the robotic arm 12, depressing button 22 may move the arm in one direction and depressing button 26 may move the arm in an opposite direction. Likewise, when the electrocautery device 14 or laser 16 are coupled to the input device 20, depressing button 30 may energize the devices, and so forth and so on. Although a foot pedal is shown and described, it is to be understood that the input device 20 may be a hand controller, a speech interface which accepts voice commands from the surgeon, a cantilever pedal or other input devices which may be well known in the art of surgical device control.

The system 10 has a switching interface 40 which couples the input device 20 to the surgical devices 12, 14, 16 and 18. The interface 40 has an input channel 42 which is connected to the input device 20 by bus 44. The interface 40 also has a plurality of output channels 46, 48, 50 and 52 that are coupled to the surgical devices by busses 54, 56, 58, 60, 94, 96, 98 and which may have adapters or controllers disposed in electrical communication therewith and therebetween.

Such adapters and controllers will be discussed in more detail hereinbelow.

Because each device 12, 14, 16, 18 may require specifically configured control signals for proper operation, adapters 90, 92 or a controller 88 may be placed intermediate and in electrical communication with a specific output channel and a specific surgical device. In the case of the robotic arm system 12, no adapter is necessary and as such, the robotic arm system 13 may be in direct connection with a specific output channel. The interface 40 couples the input channel 42 to one of the output channels 46, 48, 50 and 52.

The interface 40 has a select channel 62 which can switch the input channel 42 to a different output channel 46, 48, 50 or 52 so that the input device 20 can control any of the surgical devices. The interface 40 may be a multiplexor circuit constructed as an integrated circuit and placed on an ASIC.

Alternatively, the interface 40 may be a plurality of solenoid actuated relays coupled to the select channel by a logic circuit. The interface 40 switches to a specific output channel in response to an input signal or switching signal on the select channel 62.

As depicted in FIG. 1, there may be several inputs to the select channel 62. Such inputs originate from the foot pedal 20, the speech interface 70 and the CPU 72. The interface 40 may have a multiplexing unit such that only one switching signal may be received at the select channel 62 at any one time, thus ensuring no substantial hardware conflicts. The prioritization of the input devices may be configured so the foot pedal has highest priority followed by the voice interface and the CPU. This is intended for example as the prioritization scheme may be employed to ensure the most efficient system. As such other prioritization schemes may be employed. The select channel 62 may sequentially connect the input channel to one of the output channels each time a switching signal is provided to the select channel 62. Alternatively, the select channel 62 may be addressable so that the interface 40 connects the input channel to a specific output channel when an address is provided to the select channel 62. Such addressing is known in the art of electrical switches.

The select channel 62 may be connected by line 64 to a dedicated button 66 on the foot pedal 20. The surgeon can switch surgical devices by depressing the button 66. Alternatively, the select channel 62 may be coupled by line 68 to a speech interface 70 which allows the surgeon to switch surgical devices with voice commands.

The system 10 may have a central processing unit (CPU) 72 which receives input signals from the input device 20 through the interface 40 and bus 55. The CPU 72 receives the input signals, and can ensure that no improper commands are being input at the controller. If this occurs, the CPU 72 may respond accordingly, either by sending a different switching signal to select channel 62, or by alerting the surgeon via a video monitor or speaker.

The CPU 72 can also provide output commands for the select channel 62 on bus 76 and receive input commands from the speech interface 70 on the same bi-directional bus 76. The CPU 72 may be coupled to a monitor 80 and/or a speaker 82 by buses 84 and 86, respectively. The monitor 80 may provide a visual indication of which surgical device is coupled to the input device 20. The monitor may also provide a menu of commands which can be selected by the surgeon either through the speech interface 70 or button 66. Alternatively, the surgeon could switch to a surgical device by selecting a command through a graphic user interface. The monitor 80 may also provide information regarding improper control signals sent to a specific surgical device 12, 14, 16, 18 and recognized by the CPU 72. Each device 12, 14, 16, 18 has a specific appropriate operating range, which is well known to the skilled artisan. As such, the CPU 72 may be programmed to recognize when the requested operation from the input device 20 is inappropriate and will then alert the surgeon either visually via the monitor 80 or audibly via the speaker 82. The speaker 82 may also provide an audio indication of which surgical device is coupled to the input device 20.

The system 10 may include a controller 88 which receives the input signals from the input device 20 and provides corresponding output signals to control the operating table 18. Likewise, the system may have adapters 90 and 92 which provide an interface between the input device 20 and the specific surgical instruments connected to the system.

In operation, the interface 40 initially couples the input device 20 to one of the surgical devices. The surgeon can control a different surgical device by generating an input command that is provided to the select channel 62. The input command switches the interface 40 so that the input device 20 is coupled to a different output channel and corresponding surgical device or adapter. What is thus provided is an interface 40 that allows a surgeon to select, operate and control a plurality of different surgical devices through a common input device 20.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A device for coupling a mechanical input device to a first surgical apparatus and a second surgical apparatus, comprising:

an interface that has an input channel configured to be coupled to a mechanical input device, a first output channel configured to be coupled to a first surgical apparatus and a second output channel configured to be coupled to a second surgical apparatus, the interface having a select channel that switches the input channel between the first output channel and the second output channel; and a speech interface receiving voice commands and providing command signals to the select channel to control the switching of the input channel between the first output channel and the second output channel such that when the mechanical input device is coupled to the input channel, the mechanical input device is operable to control either the first surgical apparatus or the second surgical apparatus depending on the command signals from the speech interface.

2. The device of claim 1, wherein the interface includes a multiplexer.

3. The device of claim 1, further comprising a central processing unit which is coupled to the speech interface and the select channel, the central processing unit operable to provide an indication of which output channel the input channel is switched to.

4. A surgical system, comprising:
   a first surgical apparatus;
   a second surgical apparatus;
   a mechanical input device;
   an interface that has an input channel coupled to the mechanical input device, a first output channel coupled to the first surgical apparatus and a second output channel coupled to the second surgical apparatus, the interface having a select channel that switches the input channel between the first output channel and the second output channel; and
   a speech interface receiving voice commands and providing command signals to the select channel to control the switching of the input channel between the first output channel and the second output channel such that the mechanical input device is operable to control either the first surgical apparatus or the second surgical apparatus depending on the command signals from the speech interface.

5. The surgical system of claim 4, wherein the mechanical input device is a foot pedal.

6. The surgical system of claim 4, wherein the first surgical apparatus is an electrocautery device.

7. The surgical system of claim 6, wherein the second surgical apparatus is a robotic arm.

8. The surgical system of claim 7, wherein the mechanical input device is a foot pedal.

9. The surgical system of claim 4, wherein the first surgical apparatus is a robotic arm.

10. The surgical system of claim 4, wherein the first surgical apparatus is a laser.

11. The surgical system of claim 4, wherein the first surgical apparatus is an operating table.

12. A method for operating a first surgical apparatus and a second surgical apparatus from a mechanical input device, comprising the steps of:
    a) providing an interface that has an input channel coupled to a mechanical input device, a first output channel coupled to a first surgical apparatus, and a second output channel coupled to a second surgical apparatus;
    b) switching the interface in response to a first voice command so that the input channel is coupled to the first output channel and the mechanical input device controls the first surgical device; and
    c) switching the interface in response to a second voice command so that the input channel is coupled to the second output channel and the mechanical input device controls the second surgical device.

13. A method comprising:
    receiving a control input from a mechanical input device;
    receiving a voice selection command;
    converting the voice selection command to a command signal; and
    switching, responsive to the command signal, the control input to one of a first surgical apparatus or a second surgical apparatus to allow for control of the respective surgical apparatus using the mechanical input device.

* * * * *